United States Patent [19]

Aguilar

[11] Patent Number: 4,632,126
[45] Date of Patent: Dec. 30, 1986

[54] BIOFEEDBACK METHOD AND APPARATUS

[75] Inventor: Arturo Aguilar, Mexico City, Mexico

[73] Assignee: Leonard Bloom, Owings Mills, Md.

[21] Appl. No.: 629,777

[22] Filed: Jul. 11, 1984

[51] Int. Cl.$^4$ .......................... A61B 5/04; A63B 71/04
[52] U.S. Cl. ..................................... 128/732; 128/689; 273/1 E
[58] Field of Search ............... 128/630, 731, 732, 733, 128/905, 668

[56] References Cited

U.S. PATENT DOCUMENTS

| | | | |
|---|---|---|---|
| 3,841,316 | 10/1974 | Meyer | 273/1 E |
| 3,890,957 | 6/1975 | Freeman | 128/732 |
| 3,893,450 | 7/1975 | Ertl | 273/DIG. 28 |
| 4,149,716 | 4/1979 | Scudder | 273/DIG. 28 |
| 4,170,225 | 10/1979 | Criglar et al. | 128/733 |
| 4,335,710 | 6/1982 | Williamson | 128/1 C |
| 4,358,118 | 11/1982 | Plapp | 273/1 GC |
| 4,461,301 | 7/1984 | Ochs | 128/732 |

Primary Examiner—Brian E. Hearn
Assistant Examiner—O. Chaudhuri
Attorney, Agent, or Firm—Leonard Bloom

[57] ABSTRACT

The new biofeedback technique permits simultaneous, preferably redundant visual and auditory presentation of any intrinsically motivating stimuli together with continous information pertaining to the physiological parameter to be controlled. Essentially, it varies the signal to noise ratio (S/N) of an audio or video signal as a function of any physiological parameter or combination of several parameters. That is, intrinsically motivating stimuli, visual and auditory, are presented through a color TV set; image and sound are initially masked by white noise, set to a level just above perception (minimum signal and maximum noise). As the experimental subject changes a certain physiological parameter, image and sound become clearer if the change occurs in the desired direction. The video signal remains synchronized at any noise level. The final S/N ratio has been utilized as an index of motivation in an experiment to evaluate the efficiency of the new technique.

20 Claims, 1 Drawing Figure

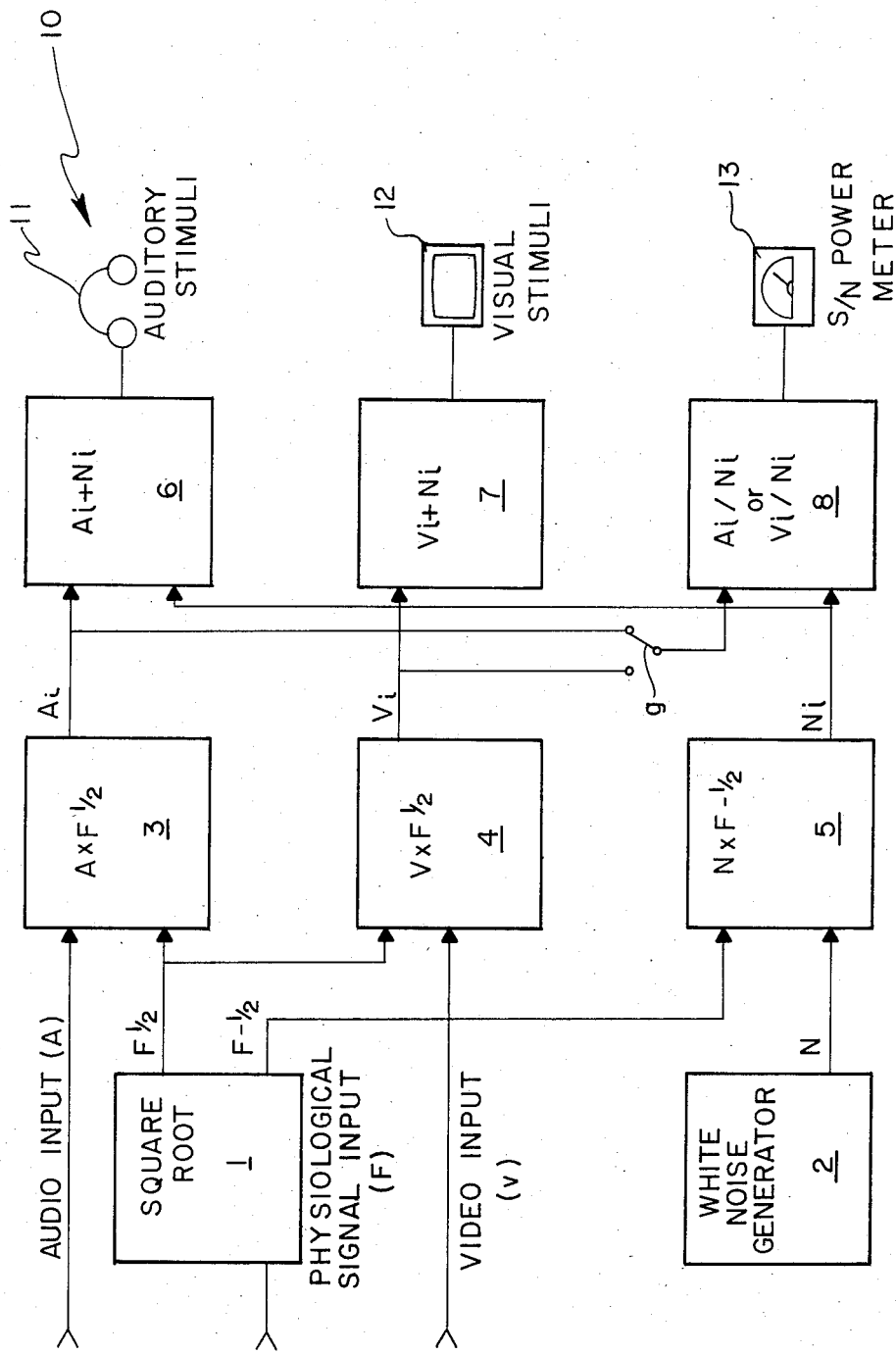

BIOFEEDBACK METHOD AND APPARATUS

BACKGROUND OF THE INVENTION

This invention relates generally to a method and apparatus for biofeedback conditioning. More particularly, this invention relates to a device having audio and visual stimuli adapted to react to at least one parameter of the subject being evaluated, an iterative process being defined thereby with the audio and visual stimuli changing as a function of patient parameter variation.

Biofeedback represents an attempt to utilize the engineering principle of feedback control on human organisms. The importance of this control, from a psychological point of view, is that the functions to be controlled are those associated with the structures that determine the emotional status of the organism. However, whereas machines have a hard wired algorithm ("drive") to reduce the error signal, humans require a "voluntary" motivational drive to develop the algorithm that achieves the goal of physiological control. Hitherto used error signal means for presenting information have not been intrinsically motivating (i.e. nobody likes or dislikes a meter needle). Since development of those algorithms in human learning requires error-signal detection through feedback (stimulus discrimination) as well as optimum drive level through feedforward (motivation), it would be more efficient to manipulate both variables through the same feedback device.

The biofeedback process can be expressed in cybernetic terms as a system (the organism) provided with an external feedback loop and a transfer function which permits the efficient perception of the functions to be controlled. A man-machine symbiosis is established in this case, because the feedback loop transfer function is performed by electronic devices. It is this utilization of technology that has made possible the development of biofeedback, because the electronic devices can perform the detection, transformation and presentation of relevant information in a faster and easier to discriminate form than that which could be obtained by the organism's own means.

The field called visceral learning is studied using a mixture of theoretical frames of references derived from operant and "classical" conditioning. It could be argued that in the same way as the neuroendochrinal control system "learns" about the organism's external environment, it can also "learn" to control the internal environment.

In cybernetic terms, learning implies control. For a response to be stable, it must be first sensed or perceived and then compared with an internal performance reference. If it is not known what the organismm is sensing, one cannot determine what is being controlled to maintain a certain response. It is this inextricable relationship between perception and control that has been misinterpreted as a direct stimulus-response relationship, but it is needed to explain the relationship between external events and behavior.

Different types of devices have been used to present visual feedback information. All of them act by changing some perceptible visual characteristic as a function of the changes of the physiological parameter to be controlled. For instance, luminous indicators that change their intensities (analogic) or different indicators that turn on and off (binary) have been used. Nevertheless, the most utilized devices have been numeric indicators, like needle meters or digital displays.

The following citations reflect the state of the art of which applicant is aware insofar as these citations appear germane to the process at hand.

U.S. Pat. No. 3,967,616, Ross
U.S. Pat. No. 3,991,304, Hillsman
U.S. Pat. No. 4,014,323, Gilmer et al
U.S. Pat. No. 4,184,485, Agoston
U.S. Pat. No. 4,246,906, Winberg et al Brener, S., Sensory and perceptual determinants of voluntary visceral control. In G. E. Schwartz and J. Beatty (Eds.), *Biofeedback Theory and Research*. New York: Academic Press, 1977.

Buckley, E. P. The man-machine system. In C. T. Morgan, A. Cahpanis, and M. W. Lund (Eds.), *Human Engineering Guide to Equipment Design*. New York: McGraw Hill, 1963.

Cornsweet, T. N. *Visual Perception*. New York: Academic Press, 1970.

Gearder, E. Control of states of consciousness. In E. Peper, S. Ancoli and M. Quinn (Eds.), *Mind/Body Interaction*. New York: Plenum Press, 1979.

Hoon, E. E. Biofeedback-assisted sexual arousal in females, a comparison of visual and auditory modalities. *Biofeedback and Self Regulation*, 1980. 5-2, 175–191.

Izard, C. E. The emergence of emotions and the development of consciousness in infancy. In J. M. Davidson and R. J. Davidson, (Eds.), *The Psychology and Consciousness*. New York: Plenum Press, 1980.

John, E. R. Multipotenciality: A statistical theory of brain function-evidence and implications. In J. M. Davidson and R. J. Davidson (Eds.), *The Psychology of Consciousness*. New York: Plenum Press, 1980.

Kimmel, H. D. The relevance or experimental studies to clinical applications of biofeedback. *Biofeedback and Self-Regulation*. Hillside, NJ: Erlbaum, 1979.

Powers, W. T. Systems approach to consciousness. In J. M. Davidson and J. R. Davidson (Eds.), *The Psychobiology of Consciousness*. New York: Plenum Press, 1980.

Stevens, S. S. Psychophysical law. In J. Cummings (Ed.), *Encyclopedia of Psychology*. New York: Herder and Herder, 1972.

Winberg et al is concerned with an apparatus for self-monitoring of physiological variables, in particular the temperature of a subject's hand. Provisions are made for the subject to hear and see respectively an audio and visual output which changes with respect to the monitored physiological variable. The termperature of the subject's fingertip is the preferred variable. The audible and visual indications are provided by a speaker 64 and a light-emitting diode 66 as shown in FIG. 1.

The patent to Agoston is concerned with a measuring arrangement for decreasing the emotional influence on instrumental diagnostical measurements which utilize a biofeedback arrangement which includes instrumentalities so that the tested person learns about the reduction in his pulse, for example, by noticing the increase in tone pitch in the audio output of the arrangement and by seeing the momentary pulse number on the dial of an indicator of the memory unit 8.

The patent to Ross proposes a multichannel system for controlling the nervous system of an organism by utilizing biofeedback. Here again, as can be seen from column 9 lines 44–48, one or more visual displays and/or auditory means such as one or more buzzers is used to indicate when the apparatus is in an inhibit mode. Thus, one set of transducing means 24 and another set of transducing means 124 are provided as portions of respective feedbacks.

Gilmer et al provides a system utilizing a low power level of pulsed alternating current for assisting a patient in producing an improved physiological or psychological condition within his body, and provides an electrotherapy treating unit with a biofeedback detecting and displaying unit for the patient's observation. Again, the stimuli defining an output from the biofeedback unit is a single pulsed frequency.

The patent to Hillsman includes preferred waveforms for breathing, monitoring of the breathing pattern, and the generation of a rectilinear raster display is employed for converting digital values in real time superimposed patterns.

None of these devices teach or render obvious either singly or in any conceivable combination that which is defined as the invention according to the instant application. The instant invention is distinguished thereover in that all of the citations are not intrinsically motivating nor more informative. In any case the only comparisons made have been between the informative properties of needle meters and digital numerical indicators, or between their binary and analogical characteristics.

In addition, auditory presentation devices have also been employed which in these cases, physiological information is presented by means of changes in intensity or frequency of pure tones (sine waves), or change in the repetition to audible "beeps". Moreover, the visual characteristics of the known prior art include observation of a needle meter or digital equivalent. There are equal lack of studies pertaining to optimum characteristics of discriminability as in the case of visual and audio stimuli. Usually the decision about which types of stimulus to utilize is arbitrary.

Biofeedback stimuli presently employed, therefore, are emotionally neuter, being neither intrinsically pleasant or aversive. Apparently, the process of control is simplified by presenting to the subject a purely informative stimulus that permits him to discriminate any change in the physiological parameters that are being controlled. Nevertheless, controlling the function implies learning and for it to occur, in addition to a discriminable stimulus, it is required that the subject be properly motivated.

The use of money as motivator has been a convenient way of standarizing the motivational level of subjects in research, be it paying them the same amount of money for their participation or giving them such amount contigent to their performance. Another motivator used in the same way as money has been the bonification of academic credits to subjects (participation is required as part of a course). For obvious reasons, the motivators mentioned cannot be used so effectively in the daily practice of biofeedback techniques (psychotherapy). In the clinical situation, the motivational problems are contemplated by the interaction between the client and the therapist.

OBJECTS AND SUMMARY OF THE INVENTION

Thus, it is a primary object of this invention to provide a feedback stimuli simultaneously discriminable and intrinsically motivating. More particularly, the use of a feedback procedure is contemplated which functions as an intrinsic reinforcer so as to provide significant advances in the application of the biofeedback technique.

While in the prior art it is known through biofeedback procedures regarding stimuli to be discriminated, few studies have investigated the effects on the rate of learning due to a change of some aspect of the feedback signal mode of presentation. Furthermore, there are not many studies where the same information has been fed back simultaneously through plural sense modalities. When different information of a symbolic nature is simultaneously presented through the visual and auditory channels, generally only one of them can be attended to. Nevertheless, comprehension of symbolic information is incremented when the same information is presented in both visual and auditory forms. This redundancy of information through two or more channels may increment the discriminability of the biofeedback signal. Taking into ccount those considerations, a series of pilot experiments and a final exploratory experiment were carried out to determine the informative and motivating and intrinsic properties of auditory and visual stimuli that could be used in biofeedback.

A device was developed which allows the presentation of stimuli, intrinsically motivating and siumltaneously informative. Furthermore, the device allows the presentation of the feedback stimuli through two sense modalities. The modalities chosen were the auditory and visual.

Accordingly, it is another object of this invention to provide a device which presents stiumli which is intrinsically motivating and simultaneously informative.

It is a further object of this invention to provide a device which allows the simultaneous presentation of feedback stimuli through two sense modalities.

It is yet a further object of this invention to provide a device in which the modalities are both auditory and visual and redundant in nature.

More specifically, the biofeedback device of the present invention is based on the masking with white noise of an auditory stimulus, such as a repeating phrase, to the point that the phrase cannot be perceived. As a certain physiological parameter changes in the desired direction, the intensity of the repeating phrase is automatically incremented while that of the noise automatically decreases; this increases intelligibility until the subject can clearly perceive the meaning of the phrase. Similarly, a visual stimulus is masked (by mixing) with visual noise (such as snow on a TV screen); the image gets clearer or less intelligible as a function of the physiological parameter.

It is a further object of this invention to provide a device and technique which is effective in the conditioning of definite human parameters such as hand temperature, heart rate, galvanic skin response, etc.

It is yet a further object of this invention to provide a device which provides the same information for both the visual and auditory processes iteratively so that there is the perception of linear response to changes in that parameter exisiting concomitantly to both the auditory and visual senses.

It is yet a further object of this invention to provide a device which benefits from such system redundancy wherein the audio and visual channels transmit the same information at least as perceived and interpreted by the subject being tested so that changes in the subject's parameter will be equally discernible both visually and auditorially.

It is a further object of this invention to provide a device as characterized above in which the motivation of the subject is enhanced both by visual and auditory means, wherein said means define a redundancy and are interrelated such that parameter changes are reflected equally by both media.

It is known that written and spoken language fulfills the requirement of being "isomorphic" and "isofunctional" information in that they are fully redundant. Accordingly, the instant device has as a further primary objective a presentation of any visual or auditory stiumli as mentioned hereinabove operated in concert and synchronized to provide redundancy similar to that which is experienced between the written and spoken word. Thus, real life, dynamic stimuli can be effective in the conditioning of physiological parameters so that isofunctionality of information fed through different sense modalities will produce a greater increase in the rate of learning due to its intrinsic redundancy.

The concomitant technological complexity required for the instant feedback device is clearly much greater than that which was previously employed on traditional devices, yet the flexibility gained makes a qualitative difference over any known prior art device since in the first place, it permits the use of any visual or auditory stimulus. Secondly, it provide for a valid, reliable and objective quantification of informative uncertainty (i.e. index of motivation) of the subject. Thus, these characteristics become possible because feedback information is presented as a signal to noise ratio (S/N). The S/N changes are determined, in turn, by those of the physiological parameters to be controlled. Moreover, the use of the S/N allows utilizing a different theoretical frame of reference for biofeedback such as information theory, in general, and signal detection theory, in particular. An associated, concomitant object and advantage at least for experimental purposes is that a 100% invariant noise stiumlus constitutes a "true" zero information control condition that could not be achieved by any other means. In other words, while visual or auditory noise is neither motivating nor informative, it does maintain occupied the corresponding sensory channel. Accordingly, it is easy to obtain an experimental control condition that is effectively equal to all others, except that the feedback information, being completely random (by white noise) is truly zero.

These and other objects will be made manifest when considering the following detailed specification when taken in conjunction with the appended drawing FIGURE.

BRIEF DESCRIPTION OF THE DRAWING

The single drawing FIGURE is a schematic block view of the apparatus according to the present invention.

BRIEF DESCRIPTION OF THE PREFERRED EMBODIMENT

Referring to the drawing now, wherein like reference numerals refer to like parts throughout the drawing FIGURE, reference numeral 10 is directed to the biofeedback apparatus according to the present invention.

More particularly, the sole FIGURE shows an audio input (A), a video input (V) and a physiological signal input (F). The physiological input (F) encounters initially a square root circuit 1 which alters the signal (F) by automatic and instantaneous modulation of the physiological signal (for example, hand temperature) which may have an output range of 0 to 4 Volts. The square root circuit also modulates this signal (F) by inversion 180° out of phase so that the output as shown in the drawing diagram is $F^{\frac{1}{2}}$ and $F^{-\frac{1}{2}}$. This corresponds to the square root of the deviation from the base line from the physiological parameter, and it is desired that the audio amplitude and video amplitude vary as a function of this signal.

Accordingly, both the audio input A and the video input V are conditioned by the square root of the physiological input (F) at stations 3 and 4 respectively so that the quantity of each of these signals has imprinted thereon variations of the physiological signal input and more particularly, the square root of the deviation from the base line of the physiological parameter. The audio output A thus conditioned is denoted as $A_i$ and the video output is similarly labeled $V_i$.

In addition, a white noise generator 2 is provided having an output N which is conditioned by the 180° out of phase signal $F^{-\frac{1}{2}}$ at station 5. The white noise generator extends itself from the audio to the video end of the frequency spectrum. Thus, the white noise signal N when treated by the signal $F^{-\frac{1}{2}}$ has an output of $N_i$. Thus, while the video and audio amplitude increases as a function of the square root of the deviation from the base line of the physilogical parameter, the amplitude of the white noise is decremented with an inverse function. Thereafter, the modulated audio signal $A_i$ is added to the modulated noise signal $N_i$ in station 6 so that the auditory stiumli 11 could be varied over such a sufficient range from total inability to perceive the auditory message to total clarity of the auditory message. Similarly, the modulated video signal was added to the modulated noise signal at station 7 and the initialized video stimuli shown on the screen 12 varies from total inability to discern the video program, to that of total clarity.

A signal to noise ratio power meter 13 is also provided which provides a ratio of the modulated audio signal to the modulated noise signal or alternatively the ratio of the modulated video signal to the modulated video noise signal at station 8. For this purpose, a switch 9 is provided allowing selection of either modulated output $A_i$ or $V_i$.

It is pertinent to mention at this point that the desired weighing of the S/N coefficient contains only those portions of the signal and the noise perceived by the human observer, with the exclusion of all video information pertinent to the intrinsic function of the television set (i.e. the compound television signal). For measurement then, it is necessary to remove all coding and synchronizing information present in the video signal and set to zero for that time interval. Of course, the same intervals of time are equally removed and set to zero in the noise signal to be mixed with the video. The procedure was realized in such a way that the integrated signal and noise energies that form the S/N ratio corresponded only to those parts visible to the human observer. On the other hand, the video monitor used for presentation of the stimuli would not have worked in the absence of that information. Therefore, that information was reintegrated after the S/N measurement stage. This procedure was not required for the auditory presentation.

It should be clear that a subject could be exposed to either stimuli separately or both stimuli simultaneously. Other forms of stimuli could equally have well be chosen. However, when more than one stiumli is provided in response to the biofeedback of a single parameter, it is desirable to synchronize the abatement or increase of the white noise (or inversely the clarity of the auditory of visual stimuli) so that which is perceived receives the same rate of change for each sense as the parameter measured changes. Additionally, in order to verify the effectiveness of this new technique, determining the kind of visual and auditory program to be employed was studied so that the auditory and visual information discerned is compatible and equal as set forth above. It is stipulated that the chosen program stimuli should produce a feeling of interest to facilitate the process of orientation and attention and to guarantee this feeling without previous subject validation. The human face and voice fulfill this requirement due to an innate preferential disposition towards these stimuli.

It was also investigated whether information which was purely informative would be as effective a feedback stimuli as stiumli which was simultaneously informative and intrinsically motivating. This was evaluated with hand temperature as the physiological parmeter to be controlled. In addition, a comparison was made between the effectiveness of simultaneous presentation of the same information to the auditory and visual channels with the effectiveness of the same information presented to each channel separately.

In one case, the auditory stiumlus, delivered by means of a pair of earphones, consisted of a voice repeatedly pronoucing a phrase masked with the white noise. The ratio of the mean power of the voice signal with respect to the noise could be varied from complete unintelligibility to complete clearness. That is, a gradual masking or distortion of the voice was produced varying the signal to voice ratio S/N depending on the increment or decrement of the variations of the physiological parameter to be controlled. In this way, the intelligibility of the voice and the amplitude of the voice represented the informative aspect of the feedback signal while the meaning of the words represented the motivational aspect.

The variation in the signal to voice relationship in the auditory presentation was made exponential (Fti the alpha when alpha=½) to produce the subjective experience of being approximately linear. This incremented the dynamic range of auditory intensity susceptible of being presented, allowing the subject's interest to be maintained for a greater range of increments.

The visual stimulus was presented through a color television screen and consisted of a human face masked or distorted with visual "noise" (snow). Visual noise is analogous to auditory noise and has been described as small blinking spots flashing over a dark field. The S/N was determined by a change of the physiological parameter, in the same manner as for the auditory stimulus. The resulting presentation may start with the screen full of visual noise, where the stimulus image was hidden "behind" the noise, barely above the threshold of perception. The sharpness of the image would increase as the subject showed a change in the physiological parameter in the desired direction. On the contrary, if the change shown occurred in the opposite direction, the sharpness of the image would deteriorate. Thus a change in S/N represented the informative aspect of the biofeedback signal, while the meaning (that the image had to the subject) represented the motivational aspect. In other words, from the point of view of the subject, the clearness and definition of the image as well as the amount in contrast in the noise was what constituted the new biofeedback information.

Due to the marked difference in the auditory and visual channels, it is also desirable to take into account the psychophysical and cognitive characteristics of the visual stiumlus. Taking these data into account, and for practical reasons, the rate of change of the visual S/N was made exponential F to the alpha where alpha=½.

For the specific example in which the parameter being monitored was that of hand temperature, the combined audio visual technique proved effective. It is clear that the written and spoken language fulfills the requirement of being isomorphic and isofunctional information since both vehicles provide the same information and are therefore fully redundant. However, providing a visual display of the written language does not necessarily harness the benefits capable of being derived from the visual stimulus as should be evident. An interesting question therefor was to determine what constitutes the same information for both visual and auditory channels, with the view towards taking advantage of a fully redundant experiment, since the information had to be interpreted by the subject as being equal, visually and auditorily. Isofunctional visual and aduitory inormation that is real dynamic stimuli are believed to be effective in the conditioning of physiological parameters. It is speculated that the isofunctionality of information fed through different sense modalities will accordingly produce a greater increase in the rate of learning due to its inherent redundancy.

Nothwithstanding, it is clear that while the technical complexity required of the new feedback device is much greater than previously employed on traditional devices, the flexibility gained makes a qualitative difference from any such prior art device since firstly it permits the use of any visual or auditory stiumlus and secondly, it provides for a valid, reliable and objective quantification of informative uncertainty (for example, the index of motivation of the subjects). These characteristics become readily identifiable because the feedback information is presented as a signal to noise ratio S/N. The S/N changes are determined in turn by those of the physiological parameter to be controlled. Furthermore, the use of the S/N ratio opens the possibility of utilizing a different theoretical frame of reference for biofeedback such as information theory in general and signal detection theory in particular. A further benefit for experimental purposes at least is that a 100% invariant noise stimulus constitutes a true zero information, controlled condition that could not be achieved by any other means. In other words, visual or auditory noise is neither motivating nor informative but it does maintain occupied the corresponding sensory channel. It is thus very easy to obtain an experimental control condition that is effectively equal to all others, except that the feedback information, being completely random white noise is truly zero.

Having thus described the invention, it should be apparent that numerous structural modifications are contemplated as being a part of this invention as set forth hereinabove and as defined hereinbelow by the claims.

What is claimed is:

1. An apparatus for making unconscious and involuntary bodily responses perceptible to at least one sense of a subject in order for the subject to manipulate said responses by conscious mental control, comprising:
   first means for providing a physiological stimulus perceptible to at least one sense of the subject;

second means for measuring the unconscious and involuntary bodily responses of the subject to the physiological stimulus;

third means for generating a noise signal in response to the measurement of the unconscious and involuntary bodily responses of the subject; and fourth means for distorting the stimulus with the noise signal generated, thereby making said unconscious and involuntary bodily responses perceptible to at least one sense of the subject, so that said responses may be manipulated.

2. The device of claim 1, wherein said first means is any auditory stimuli susceptible of presentation through an audio amplifier and speaker.

3. The device of claim 1, wherein said first means is any visual stimuli susceptible of presentation through a video monitor or television screen.

4. The device of claim 1, wherein said third means comprises a white noise generator coupled to said first means and adapted to decrease as a function of the subject's ability to manipulate the unconscious and involuntary bodily response desired in a chosen direction, whereby said first means becomes clearer to the subject.

5. The device of claim 2, wherein said third means comprises a white noise generator coupled to said first means and adapted to decrease as a function of the subject's ability to manipulate the unconscious and involuntary bodily response desired in a chosen direction, whereby said first means becomes clearer to the subject.

6. The device of claim 3, wherein said third means comprises a white noise generator coupled to said first means and adapted to decrease as a function of the subject's ability to manipulate the unconscious and involuntary bodily response desired in a chosen direction, whereby said first means becomes clearer to the subject.

7. The device of claim 6, wherein said first means further comprises an audio input, and wherein said second means is in the form of a physiological signal input, the numeric value for which is modified by taking the square root thereof, a quantity thus derived multiplied by said audio input, said same quantity is similarly modified by a video input, an inverse of the square root of said quantity is multiplied by a signal from the white noise generator, the output of which is added respectively to the modified auditory input and the modified visual input, whereby auditory and visual stimuli are conditioned by said white noise generator and the subject's ability to alter said second means, and means for denoting the ratio of said auditory signal applied and said visual signal applied as a function of said white noise generator signal conditioned by said inverse of said physiological signal input.

8. An improvement in a biofeedback system comprising, in combination:

a parameter measuring means adapted to monitor change in at least one unconscious and involuntary physiological characteristic of a subject, means providing a stimuli to the subject, and a stimuli enhancing means coupled operatively to said measuring means and to said stimuli providing means and including means for generating a noise signal to vary discernability of said stimuli, whereby incentive is provided to increase discernability of said stimuli for biofeedback conditioning.

9. The device of claim 8, wherein said stimuli providing means is any auditory stimuli.

10. The device of claim 8, wherein said stimuli providing means is any visual stimuli.

11. The device of claim 8, wherein said means for generating a noise signal is a white noise generator signal coupled to said stimuli providing means and adapted to decrease as a function of the subject's ability to manipulate the characteristic desired in a chosen direction, whereby said stimuli providing means becomes clearer to the subject.

12. A method for enhancing biofeedback conditioning including the steps of:

measuring at least one unconscious and involuntary physiological parameter of the subject to be conditioned, deriving a voltage signal corresponding to the measurement, with a source of stimuli to be imparted to one of the senses of the subject, distorting the source of stimuli with a noise signal and lowering the distortion in response to control of the parameter by the subject.

13. The method of motivating a subject to control an unconscious and involuntary physiological parameter of the subject's body, comprising the steps of providing a stimulus to be sensed by the subject, measuring the physiological parameter, generating a noise signal in response to the measurement of the parameter, and using the noise signal to distort the stimulus, such that the stimulus becomes clearer as the physiological parameter is controlled by the subject.

14. The method of claim 13, wherein the stimulus comprises a visual signal presented on a television set viewed by the subject.

15. The method of claim 13, wherein the stimulus comprises an audio signal heard by the subject.

16. The method of motivating a human subject to control an unconscious and involuntary physiological parameter of the subject's body, comprising the steps of allowing the subject to both view a video signal on a television screen and simultaneously listen to an audio signal, detecting and measuring the physiological parameter, generating a noise signal in response to the measurement of the parameter, and using the noise signal to distort the video and audio signals; such that as the parameter is controlled by the subject, the noise signals are reduced to reduce the distortion, and the visual and audio signals become clearer to the subject.

17. A biofeedback system to assist a subject to control at least one unconscious and involuntary physiological parameter of the subject's body, comprising, in combination, means for providing at least one stimulus to be imparted to one of the subject's senses, means for measuring the physiological parameter of the subject and obtaining a signal in response thereto, a noise generator for obtaining a noise in response to the signal from the parameter being measured, and means for distorting the stimulus in accordance with the noise; such that as the subject controls the physiological parameter being measured, the noise is reduced and the stimulus imparted to the subject becomes less distorted.

18. In a biofeedback system, wherein at least one unconscious and involuntary physiological parameter of a subject is being monitored and is intended to be controlled by the subject using biofeedback, the improvement which comprises means for providing a signal to be sensed by the subject, means for generating noise in response to the physiological parameter being monitored, means for mixing the noise with the signal, thereby providing a signal-to-noise ratio and distorting the signal, and means for varying the signal-to-noise ratio in accordance with the parameter being monitored, such that the signal-to-noise ratio will be increased and the distortion decreased as the subject controls the physiological parameter using biofeedback.

19. In a biofeedback method, wherein at least one unconscious and involuntary physiological parameter of a subject is being monitored and is intended to be controlled by the subject using biofeedback, the improvement which comprises, in combination, providing a signal to the subject, mixing the signal with noise, thereby providing a signal-to-noise ratio, setting the signal-to-noise ratio just above minimum perception of the signal by the subject, and varying the signal-to-noise ratio in accordance with the physiological parameter being monitored, whereby as the subject controls the physiological parameter, the signal-to-noise ratio will be increased and the signal will become clearer, thereby motivating the subject to control the physiological parameter using biofeedback.

20. A method of making unconscious and involuntary bodily responses perceptible to at least one sense of a subject in order for the subject to manipulate said responses by conscious mental control, comprising:
first, providing a physiological stimulus perceptible to at least one sense of the subject;
second, measuring the unconscious and involuntary bodily responses of the subject to the physiological stimulus;
third, generating a noise signal in response to the measurement of the unconscious and involuntary bodily responses of the subject; and
fourth, distorting the stimulus with the noise signal generated, thereby making said unconscious and involuntary bodily responses perceptible to at least one sense of the subject, so that said responses may be manipulated.

* * * * *

UNITED STATES PATENT AND TRADEMARK OFFICE
CERTIFICATE OF CORRECTION

PATENT NO. : 4,632,126

DATED : December 30, 1986

INVENTOR(S) : Aguilar

It is certified that error appears in the above-identified patent and that said Letters Patent are hereby corrected as shown below:

On the first page or title page, under "assignee", Leonard Bloom , part interest.

In column 2, line 51, change "termperature" to --- temperature --- .

In column 5, line 38, change "stiumlus" to --- stimulus --- .

In column 6, line 67, change "stiumli" to --- stimuli --- .

In column 8, lines 22 and 23, change "aduitory inormation" to --- auditory information --- .

In column 8, line 35, change "stiumlus" to --- stimulus --- .

Signed and Sealed this

Twenty-fifth Day of August, 1987

*Attest:*

DONALD J. QUIGG

*Attesting Officer*     *Commissioner of Patents and Trademarks*